United States Patent [19]

Mattson et al.

[11] Patent Number: 5,595,993
[45] Date of Patent: Jan. 21, 1997

[54] ANTISCHEMIC PIPERAZINYL- AND PIPERIDINYL-CYCLOHEXANES

[75] Inventors: Ronald J. Mattson, Meriden; John D. Catt, Southington, both of Conn.

[73] Assignee: Bristol-Myers Squibb Company, New York, N.Y.

[21] Appl. No.: 306,081

[22] Filed: Sep. 14, 1994

Related U.S. Application Data

[60] Division of Ser. No. 82,587, Jun. 25, 1993, Pat. No. 5,352,678, which is a continuation-in-part of Ser. No. 848,767, Mar. 11, 1992, abandoned.

[51] Int. Cl.$^6$ ............... A61K 31/495; A61K 31/445; C07D 211/08; C07D 411/00
[52] U.S. Cl. ............... 514/255; 514/317; 514/321; 544/377; 544/398; 544/403; 546/192; 546/197; 546/236
[58] Field of Search ............... 514/255, 321, 514/317; 546/197, 192, 236; 544/377, 403, 398

[56] References Cited

U.S. PATENT DOCUMENTS

| | | | |
|---|---|---|---|
| 4,954,502 | 9/1990 | Smith et al. | 514/253 |
| 4,975,445 | 12/1990 | Coprathe et al. | 514/252 |
| 5,071,551 | 12/1991 | Buschmann et al. | 514/238.8 |
| 5,281,595 | 1/1994 | Lange et al. | 514/253 |
| 5,332,743 | 7/1994 | Baxter et al. | 514/255 |
| 5,356,891 | 10/1994 | Witiak et al. | 514/212 |
| 5,364,867 | 11/1994 | Hadkins et al. | 514/526 |

OTHER PUBLICATIONS

Borer et al, "An Asymmetric Synthesis of a 3-Hydroxy-beta-lactam by Ketene-imine Cycloaddition: Utilization of χ Chiral Ketenes from Carbohydrates", *Tetrahedron Letters*, vol. 32, No. 8, (1991) pp. 1039–1040.
*Chemical Abstracts*, 106: 11951c, (1987).

*Primary Examiner*—C. Warren Ivy
*Assistant Examiner*—Raymond Covington
*Attorney, Agent, or Firm*—Sandra M. Nolan

[57] ABSTRACT

Piperidinyl-substituted cyclohexanes of Formula I have antiischemic properties:

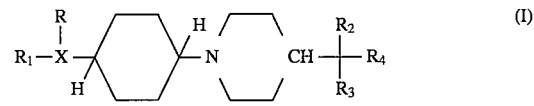

wherein $R=R_1$ and is independently H or halogen; or R and $R_1$ may be taken together to form an —$O(CH_2)_mO$— (m=1 or 2);

X=a phenyl residue;

$R_2=R_3$ and is independently H or $C_{1-4}$ alkyl; and $R_4$=phenyl or substituted phenyl wherein the phenyl group is mono-, or di-substituted with groups selected from: F, Cl, I and $C_{1-4}$ alkoxy.

12 Claims, No Drawings

ANTISCHEMIC PIPERAZINYL- AND PIPERIDINYL-CYCLOHEXANES

CROSS-REFERENCE TO RELATED APPLICATION(S)

This is a division of application Ser. No. 08/082,587 filed: Jun. 25, 1993, U.S. Pat. No. 5,352,678, which was a continuation-in-part of U.S. Ser. No. 07/848,767, filed Mar. 11, 1992 abandoned.

BACKGROUND

This invention generally pertains to piperazinyl- and piperidinyl-cyclohexanes having anti-ischemic, antipsychotic and other bio-affecting properties and to their preparation and use. In some preferred embodiments, the invention is concerned with 1,4-disubstituted piperazine or piperidine derivatives wherein the 4-substituent is benzyl or substituted benzyl, and the 1-substituent is a 4-arylcyclohexan-1-yl moiety. These compounds, and others structurally related thereto, possess a unique profile that makes them useful in the treatment of ischemia-induced illnesses and psychosis.

Caprathe et al., in U.S. Pat. No. 4,975,445, disclosed a series of piperazinyl-cyclohexene compounds characterized by structural formula A:

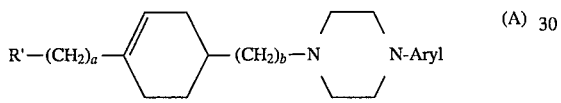

wherein R' is an aryl or heterocyclic ring, a is 0–2 and b is 0–4.

As can be seen, these earlier compounds are chemically distinguishable from the instant compounds on the basis of their chemical structures because they are aryl- or heteroaryl-piperazines, whereas the instant compounds are benzyl- or heteroarylmethyl-piperazines (when, in Formula I below, Y=N) or -piperidines (when, in Formula I below, Y=CH).

U.S. Pat. No. 4,954,502 to Smith et al discloses compounds of the following formula:

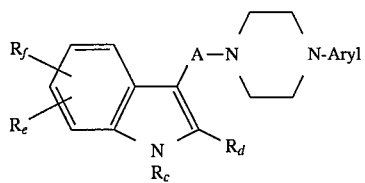

wherein A may be a $C_{5-7}$ cycloalkyl ring. The compounds are taught to be antidepressants. There is no suggestion in the patent that these compounds are useful in the treatment of stroke or other ischemia-based conditions.

Caprathe et al disclosed a series of piperazinyl-cyclohexanol compounds characterized by structural formula B in U.S. Pat. No. 4,957,921. Formula B is:

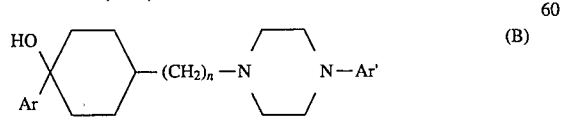

wherein n is 0 to 4 and Ar and Ar' are aryl or heterocyclic rings. These compounds are structurally distinguishable from the instant compounds. The reference compounds are aryl-piperazines, while the instant compounds are benzyl- or heteroarylmethyl-piperazines.

SUMMARY AND DETAILED DESCRIPTION OF THE INVENTION

In its broadest aspect, the invention is concerned with certain dopaminergic compounds which are substituted benzyl- or heteroarylmethyl-piperazinyl cyclohexanes or substituted benzyl or heteroarylmethyl-piperidinyl cyclohexanes which are useful anti-ischemic and antipsychotic agents. The compounds conform to formula I:

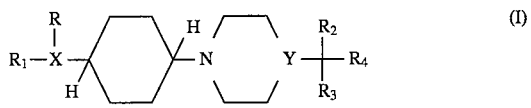

wherein

R=$R_1$ and is independently H or halogen; or R and $R_1$ may be taken together to form an —O(CH$_2$)$_m$O— (m=1 or 2);

X=a phenyl residue;

Y=N or CH;

$R_2$=$R_3$ and is independently H or $C_{1-4}$ alkyl; and $R_4$=phenyl or substituted phenyl, wherein the phenyl group is mono-, on di-substituted with groups selected from: F, Cl, and $C_{1-4}$ alkoxy.

Compounds of formula I include all pharmaceutically acceptable salts and/or solvates (e.g., hydrates) thereof. The invention also encompasses all stereoisomers of compounds of formula I.

Pharmaceutically acceptable salts based on Formula I can be obtained using inorganic or organic acids such as oxalic, sulfuric, phosphoric, hydrochloric, hydrobromic, hydroiodic, citric, acetic, benzoic, fumaric, cinnamic, mandelic, nitric, mucic, isethionic, palmitic, heptanoic and the like.

R and $R_1$ may be H or a halogen moiety.

One preferred group of R substituents are halogen atoms. While R may be Cl, Br, I or F, it is highly preferred that it be F.

In another preferred group of compounds, R and $R_1$ may be taken together to form an —O(CH$_2$)$_m$ O— (m=1 or 2) moiety. When m=1, a benzodioxyl moiety is formed.

X is a phenyl group.

Y may be N or CH. While it may be either, the use of piperidines (wherein Y=CH) is somewhat preferred.

$R_2$ and $R_3$ may each independently be selected from H and $C_{1-4}$ alkyl groups.

$R_4$ may be a phenyl or substituted phenyl group bearing 1 or 2 substituents, with the substituents chosen from: F, Cl, and $C_{1-4}$ alkoxy.

Preferred compounds of Formula I include:

cis 1-[(2-chlorophenyl)methyl]-4-[4-(4-fluorophenyl)-1-cyclohexyl]piperazine;

trans 1-[(2-chlorophenyl)methyl]-4-[4-(4-fluorophenyl)-1-cyclohexyl]piperazine;

trans 1-[4-(4-fluorophenyl)-1-cyclohexyl]-4-[(2,5-difluorophenyl)methyl]piperazine;

trans 1-[4-(1,3-benzodioxol-5-yl)-1-cyclohexyl]-4-[(3-methoxyphenyl)methyl]piperazine;

trans 1-[4-(1,3-benzodioxol-5-yl)-1-cyclohexyl]-4-[(2,5-difluorophenyl)methyl]piperazine;

trans 1-[4-(1,3-benzodioxol-5-yl)-1-cyclohexyl]-4-[(2-chlorophenyl)methyl]piperazine;

trans 1-[4-(1,3-benzodioxol-5-yl)-1-cyclohexyl]-4-[(2,5-difluorophenyl)methyl]piperidine;

trans 1-[4-(4-fluorophenyl)-1-cyclohexyl]-4-[(2-fluoro-5-methoxyphenyl)methyl]piperidine;

trans 1-[4-(4-fluorophenyl)-1-cyclohexyl]-4-[(2,5-difluorophenyl)methyl]piperidine; and trans 1-[4-(1,3-benzodioxol-5-yl)-1-cyclohexyl]-4-[(2-fluoro-5-methoxyphenyl)methyl]piperidine and the like.

The compounds of the present invention are useful pharmacologic agents with anti-ischemic properties. Brain cells are particularly vulnerable to damage caused by ischemic conditions. Brain ischemia, or insufficient oxygen, may result from injury or disease and may last from only transient periods of time to periods of lengthy duration, as in stroke.

In this regard, the compounds of Formula I are useful for treatment and prevention of injury to the brain and spinal cord and of edema due to head trauma, stroke, arrested breathing, cardiac arrest, Reyes syndrome, cerebral thrombosis, embolism, hemorrhage or tumors, encephalomyelitis, spinal cord injury, hydroencephalitis, and post-operative brain injury.

By "dopaminergic", applicants mean exhibiting activity at dopamine ($D_2$) receptor sites. The binding test employed is set out below Table 1.

Table 1 shows the structures of some Formula I compounds.

TABLE 1

Anti-ischemic Dopaminergic compounds of Formula I

| A | Cyclohexane: cis/trans | Y | A' |
|---|---|---|---|
| 4-F-phenyl | cis | N | 2-Cl-benzyl |
| 4-F-phenyl | trans | N | 2-Cl-benzyl |
| 4-F-phenyl | trans | N | 2,5-diF-benzyl |
| 1,3-benzodioxol-5-yl | trans | N | 2-OCH₃-benzyl (2-OCH3, then CH2) |
| 1,3-benzodioxol-5-yl | trans | N | 2-Cl-benzyl |
| 1,3-benzodioxol-5-yl | trans | N | 2,5-diF-benzyl |

TABLE 1-continued

Anti-ischemic Dopaminergic compounds of Formula I

| A | Cyclohexane: cis/trans | Y | A' |
|---|---|---|---|
| benzodioxole | trans | CH | 2,4-difluorophenyl-CH₂– |
| 4-fluorophenyl | trans | CH | 2-fluoro-4-methoxyphenyl-CH₂– |
| 4-fluorophenyl | trans | CH | 2,4-difluorophenyl-CH₂– |
| benzodioxole | trans | CH | 2-fluoro-4-methoxyphenyl-CH₂– |

In vitro $IC_{50}$ test values for binding to the $D_2$ receptor were determined for representative compounds of Formula I by the method of Burt, Creese, and Snyder, *Molecular Pharmacology* 12, 800 (1976); Creese, Burt, and Snyder, *Science* 196, 326 (1977); and Creese, Burt and Snyder, *Science* 192, 481 (1976).

The compounds comprising the present invention are selective agents at the sigma receptor. It has been suggested that specific sigma antagonists are an interesting approach in the development of new anti-ischemic agents [see: D. Lobner and P. Lipton: *Neurosci. Lett.* 117, 169–174 (1990); and T. S. Rao, et. al., *Neuropharmacology* 29, 1199–1204 (1990b)]. Furthermore, there is evidence that sigma agents may be useful in the treatment of psychosis [see: Su, T. P.: *Neurosci. Lett.* 71: 224–228 (1986)]. Compounds of the present invention are thus envisioned to be useful in the treatment of psychosis, as well as in the treatment of brain ischemia.

In vitro $IC_{50}$ test values for binding to the sigma receptor were determined for representative compounds of Formula I by the method of Tam and Cook [see: Tam, S. W., and Cook, L: *Proc. Natl. Acad. Sci. USA* 81, 5618–5621 (1984)] with only minor modifications. Test $IC_{50}$ values lower than 100 nM are considered to reflect activity at the sigma receptor. Compounds with $IC_{50}$ values lower than 40 nM comprise the preferred compounds.

The anti-ischemic activity of the compounds of Formula I has been demonstrated in certain pharmacological tests and model systems that are used to determine drug effects on brain ischemia and its aftermath. Most specifically, administration of the compounds of Formula I results in protection against hypoxia-induced death in an anoxic nitrogen test in rats (See below). The test identifies the neuro-protective effects of substances against lethal brain damages produced by a lack of oxygen consumption (anoxia). In this test procedure, control animals exposed for one minute to a pure nitrogen atmosphere will expire because of respiratory failure caused by irreversible damage to the brain respiratory center. To demonstrate effectiveness, experimental compounds must antagonize the anoxic insult, increasing the survivability of the test animals.

The anoxic nitrogen test is an in vivo model of brain ischemia in rats [see: Wauquier, A., et al: *Arch. Int. Pharmacodyn.*, 249, 330–334 (1981); Wauquier A., et al: *Drug Dev. Res.*, 8, 373–380 (1986))]. Compounds of the present invention are active in this in vivo model of brain ischemia when given subcutaneously in 10 mg/kg doses, thus providing additional evidence that the present compounds will be useful in the treatment of brain ischemia.

The anoxic nitrogen test procedure was:

The animals utilized are male Sprague-Dawley rats (200–400 grams) housed four animals per cage in a normal controlled environment with unlimited access to food and water. Usually there are 8 animals per dose, however, 4 animals can be employed to obtain an initial impression of a compound's activity.

Animals are parenterally or orally administered the vehicle or test compound 30 minutes before the anoxic insult. The anoxic episode consists of placing up to 8 animals in the sealed test chamber (10" l×10" w×6" h) continuously flushed with pure $N_2$ (4.5 grade) at a flow rate of 5 SCFM for 1 min. Animals are then promptly removed to normal atmosphere and observed for the 2 hour period. Typically, animals become disoriented within 15 seconds after which they remain motionless.

Even though the heart is still beating after the $N_2$ exposure, all control animals fail to gasp when removed from the chamber and usually expire within 3 minutes. Drug treated animals, however, still gasp or start gasping after being removed from the chamber which is a good indication is an animal will survive the $N_2$ exposure.

Results are recorded as:

(Number of animals surviving (2 hr))/(Number of animals tested)×100%.

One aspect of the present invention provides a method for treating a mammal suffering from ischemia or being susceptible to ischemia, which comprises administering systematically to said mammal a therapeutically effective amount of a compound of Formula I or a pharmaceutically acceptable acid addition salt thereof.

Although the dosage and dosage regimen must in each case be carefully adjusted, utilizing sound professional judgement and considering the age, weight and condition of the recipient, the route of administration and the nature and gravity of the illness, generally the daily dose will be from about 0.01 to about 10 mg/kg, preferable 0.1 to 2 mg/kg, when administered parenterally and from about 1 to 50 mg/kg, when administered orally. In some instances a sufficient therapeutic effect can be obtained at lower doses while in others, greater doses will be required.

Systemic administration refers to oral, rectal, transnasal, transdermal, and parenteral (i.e., intramuscular, intravenous, and subcutaneous). Generally it will be found that when a compound is administered orally, a greater quantity of the active agent is required to produce the same effect as a similar quantity given parenterally. According to good clinical practice, it is preferred to administer the present compounds at a concentration level that will produce effective anti-ischemic effects without causing any harmful or untoward side effects.

The compounds of the present invention may be administered for anti-ischemic or antipsychotic purposes either as individual therapeutic agents or as mixtures with other therapeutic agents. Therapeutically, they are generally given as pharmaceutical compositions composed of an anti-ischemic or antipsychotic amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g., starch) and wetting agents (e.g., sodium lauryl sulfate). Solutions or suspensions of a Formula I compound with conventional pharmaceutical vehicles are employed for parenteral compositions such as aqueous solution for intravenous injection or an oily suspension for intramuscular injection. Compounds of Formula I can be prepared by the processes set out in the following schemes:

The preferred syntheses of the 1-(4-arylcyclohexyl)-4-(arylmethyl)piperazines and 1-(4-arylcyclohexyl)-4-(arylmethyl)piperidines, i, are shown in Schemes 1 and 2.

SCHEME 1

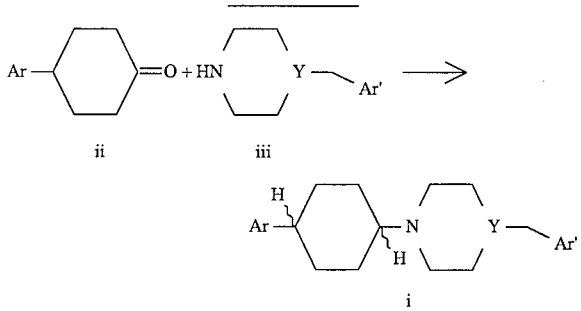

The intermediate 4-arylcyclohexanones, ii, (Lednicer et al, *J. Med. Chem.*, 1975, 5, 1235), are condensed (Scheme 1) with the appropriately substituted 4-(arylmethyl)piperazines or 4-(arylmethyl)piperidines iii under reductive alkylation conditions such as titanium isopropoxide/NaBH$_4$, sodium cyanoborohydride, sodium triacetoxyborohydride, and the like, to provide the products, i. The condensation provides isomeric mixtures of the products, i. The isomeric products may be separated by methods known to those skilled in the art which include, but are not limited to, recrystallization and chromatography using absorbants of silica (silica gel), aluminium oxide (alumina) and the like.

SCHEME 2

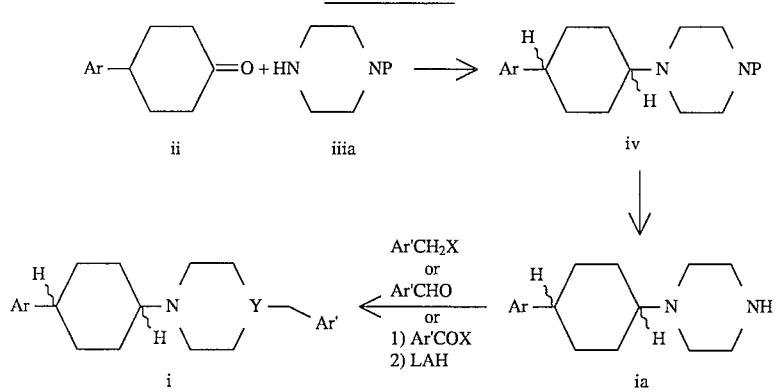

Alternatively, the 1-(4-arylcyclohexyl)-4-(arylmethyl)piperazines, i (Y=N), may be prepared by condensation of the 4-arylcyclohexanones, ii, with an appropriately protected piperazine iiia as shown in Scheme 2. Suitable protecting groups for the piperazine include, but are not limited to, carbobenzyloxy, ethyl carbamate, methyl carbamate, t-butyl carbamate, formyl, acetyl, propionyl, methanesulfonyl, ethanesulfonyl, benzenesulfonyl, para-toluenesulfonyl, benzyl, appropriately substituted benzyl, and the like. Highly preferred protecting groups are the t-butyl carbamate and the carbobenzyloxy group. The condensation provides isomeric mixtures of the intermediates, iv, which are separated as described above and deprotected to give the intermediates, ia. Methods suitable for deprotection include, but are not limited to, acidic or basic hydrolysis, hydrazinolysis, hydrogenolysis, solvolysis, and the like.

The 4-(4-arylcyclohexyl)-1-(arylmethyl)piperazines i (Y=N) may then prepared by alkylation of intermediate ia with suitable alkylating agents such as arylmethyl halides, arylmethyl para-toluenesulfonates, arylmethyl methanesulfonates, and the like, in the presence of a base in a suitable solvent such as acetonitrile, tetrahydrofuran, dioxane, acetone, 1,2-dichloroethane, dimethylformamide, dimethyl sulfoxide, and the like, at temperatures of 25° C. to 130° C. Suitable bases for this reaction include, but are not limited to, sodium or potassium carbonate, sodium or potassium bicarbonate, sodium or potassium hydride, sodium or potassium hydroxide, diisopropylethylamine, pyridine, and the like.

Alternately, the 1-(4-arylcyclohexyl)piperazines ia may be reductively coupled with aryl aldehydes and ketones to provide 1-(4-arylcyclohexyl)-1-(arylmethyl)piperazines i (Y=N). Reagents suitable for this reductive coupling include, but are not limited to, sodium borohydride, sodium cyanoborohydride, sodium triacetoxyborohydride, sodium triacetoxyborohydride/acetic acid, sodium borohydride/titanium isopropoxide, sodium cyanoborohydride/titanium isopropoxide, and the like. The reductive coupling is generally run in a solvent such as ethanol, methanol, tetrahydrofuran, dioxane, dichloromethane, 1,2-dichloroethane, dimethoxyethane, and the like, at temperatures of 25° C. to 100° C.

The 4-(4-arylcyclohexyl)-1-(arylmethyl)piperazines i (Y=N) may also be prepared by coupling the intermediates, ia, with an aryl carboxylic acid derivative to furnish an aryl carboxamide, which can then be reduced to give the products, i. Typical acid derivatives include, but are not limited to, acid chlorides, esters, suitable activated amides such as acyl imidazoles, and the like. The carboxamides may be reduced with the usual reagents, which include, but are not limited to, lithium aluminum hydride, diisobutyl aluminum hydride, diborane, sodium bis(2-methoxyethoxy)aluminum hydride, and the like. The reduction is typically carried out in a solvent such as tetrahydrofuran, diethyl ether, dioxane, benzene, toluene, cyclohexane, and the like, from temperatures of 0° C. to 120° C. Other methods known to those skilled in the arts for the preparation and reduction of amides may also be used. An alternate synthesis of the 4-(4-arylcyclohexyl)-1-(arylmethyl)piperazines and 1-(4-arylcyclohexyl)-4(arylmethyl)piperidines i is shown in Scheme 3. The intermediate substituted cyclohexanones, vi, may be prepared by condensation of cyclohexane-1,4-dione monoethylene ketal v with a 1-arylmethylpiperazine or 4-arylmethylpiperidine iii under reductive alkylation conditions such as titanium isopropoxide/NaBH4, sodium cyanoborohydride, sodium triacetoxyborohydride/acetic acid, and the like, as described in Scheme 1. The resulting ketals are cleaved under acidic conditions such as, acetone/HCl, THF/HCl, ethanol/HCl, ethanol/H₂SO₄, methanol/HCl, acetone/H₂SO₄, THF/H₂SO₄, and the like to provide the intermediate cyclohexanes vi. Other methods known to those skilled in the art may also be used.

SCHEME 3

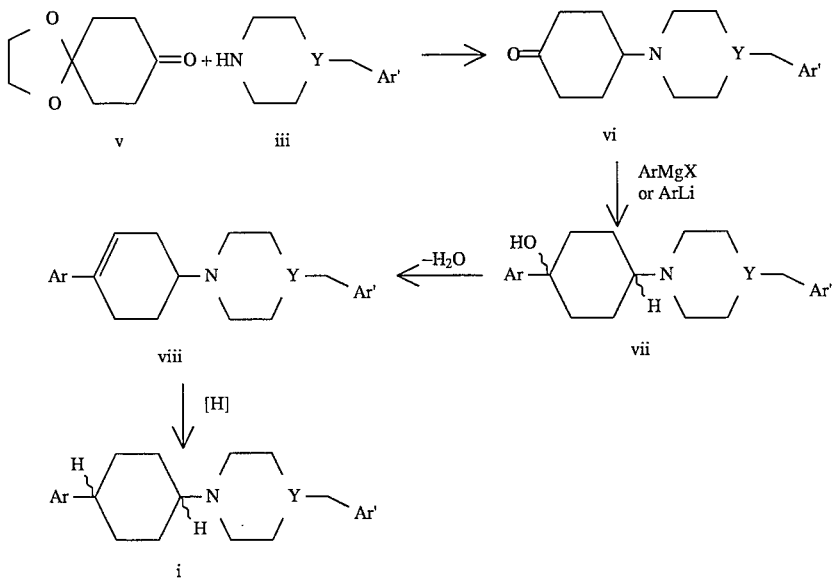

The further addition of organometallic reagents such as, Grignard reagents or organolithium reagents, and the like, to the intermediates, vi, provides the 1-aryl-4-(arylmethyl-1-piperazinyl)cyclohexanols and the 1-aryl-4-(arylmethyl-1-piperidinyl)cyclohexanols, vii, as mixtures of isomers. The reaction may be carried out in an appropriate solvent such as tetrahydrofuran, diethyl ether, dimethoxyethane, diethyleneglycol dimethyl ether, and the like, at temperatures from −100° C. to 25° C. The isomers may be separated and the individual isomers reacted separately or the isomer mixture may be used in the following procedure. Means for separation of the isomers are described in Scheme 1 above.

Dehydration of the intermediates, vii, provides the compounds of formula viii. Dehydration may be accomplished by heating with thionyl chloride, phosphorus oxychloride, thionyl bromide, phosphorus oxybromide, phosphorus trichloride, phosphorus tribromide, phosphorus pentachloride, phosphorus tribromide, and the like, in an inert solvent such as dichloromethane, 1,2-dichloroethane, chloroform, carbon tetrachloride, benzene, cyclohexane and the like at temperatures of 20° C. to 80° C. Additionally the dehydration may be accomplished by reacting with trifluoroacetic acid/trifluoroacetic anhydride, trifluoroacetic acid, phosphorus oxychloride/pyridine, para-toluenesulfonic acid/toluene, methanesulfonic acid/cyclohexane, sodium hydrogen sulfate/toluene, methanesulfonic acid/toluene, and the like, at temperatures from 0° C. to 110° C. Other methods for the dehydration of alcohols known to those skilled in the art may also be used. Alternatively, the crude diastereomer mixture from the reaction of the organometallic reagent and the 4-(4-arylmethyl-1-piperazinyl)cyclohexanones and 4-(4-arylmethyl-1-piperidinyl)-cyclohexanones may be dehydrated directly under acidic conditions as described above.

Reduction of the compounds, viii, provides the 1-(4-arylcyclohexyl)-4-(arylmethyl)piperazines and 1-(4-arylcyclohexyl)-4-(arylmethyl)-piperidines, i, as shown in Scheme 3. This reduction may be accomplished either chemically or catalytically by means known to those skilled in the art. The preferred catalytic method is reduction with platinum oxide in acetic acid. Other catalysts suitable for this reduction include palladium on carbon, platinum on carbon, palladium hydroxide (Pearlman's catalyst), Raney nickel and rhodium on carbon in solvents such as methanol, ethanol, 2-propanol, acetic acid, dioxane, tetrahydrofuran, dimethylformamide, dimethoxyethane, and the like, at temperatures from 20° to 80° C. Typical chemical reducing agents for this reduction include, but are not limited to, $LiAlH_4$, $AlH_3$, borane, or complexes of borane with common tertiary amines or with common sulfides (methyl sulfide, ethyl sulfide, etc). The chemical reductions are generally carried out in solvents such as tetrahydrofuran, diethyl ether, dioxane, and the like, at temperatures of 0° C. to 150° C. The products, i, are obtained as mixtures of isomers which are separated as described in Scheme 1 above.

Scheme 4 shows an alternate synthesis of the 4-(4-arylcyclohexyl)-1-(arylmethyl)piperazines (Y=N) i by way of intermediate viiia. The intermediate substituted 4-aryl-4-hydroxycyclohexanones ix are obtained by addition of organometallic reagents such as Grignard reagents, organolithium reagents, and the like, to 1,4-cyclohexanedione mono-ethylene ketal as described in Scheme 3. The ketals are cleaved under acidic conditions in a solvent such as methanol, ethanol, 2-propanol, acetone, tetrahydrofuran, dioxane, dimethoxyethane, acetonitrile, dichloromethane, 1,2-dichloroethane, and the like, to give the 4-aryl-4-hydroxycyclohexanones ix. Acids suitable for this hydrolysis include, but are not limited to, hydrochloric, sulfuric, acetic, dichloroacetic, trifluoroacetic, phosphoric, para-toluenesulfonic, methanesulfonic, benzoic, and the like.

Intermediates ix can be reductively coupled with a mono-protected piperazine iiia, using conditions as described above in Scheme 1 to give the 1-protected piperazine intermediate, viia. Suitable protecting groups for the piperazine are described in Scheme 2 above. The intermediates, viia, are readily dehydrated and deprotected to provide the 1-(4-aryl-3-cyclohexen-1-yl)piperazines, viiia, using conditions as described above. Highly preferred for this dehydration is treatment with trifluoroacetic acid which may result in simultaneous removal of the piperazine protecting group. Other methods for deprotection of the piperazine are described in Scheme 2 above.

The 1-(4-aryl-3-cyclohexen-1-yl)-4-arylmethylpiperazines, viii, are prepared by alkylation of intermediate viiia with alkylating agents as described in Scheme 3 above. Alternately, the 1-(4-aryl-3-cyclohexen-1-yl)piperazines viiia may be reductively coupled with aryl aldehydes and ketones to provide 1-[4-aryl(alkyl)-3-cyclohexen-1-yl]-1-(arylmethyl)piperazines i (Y=N) as described in Scheme 2 above. The 1-(4-aryl-3-cyclohexen-1-yl)-1-(arylmethyl)piperazines, viii, may also be prepared by coupling the intermediates, viiia, with an aryl carboxylic acid derivative to furnish an aryl carboxamide, which can then be reduced to give the products, i (Y=N) as described in Scheme 2 above. Reduction of the compounds, as previously discussed in Scheme 2, viii, provide the 1-(4-arylcyclohexyl])4-(arylmethyl)piperazines i.

EXAMPLES

The compounds which constitute this invention, their methods of preparation and their biological actions will be

SCHEME 4

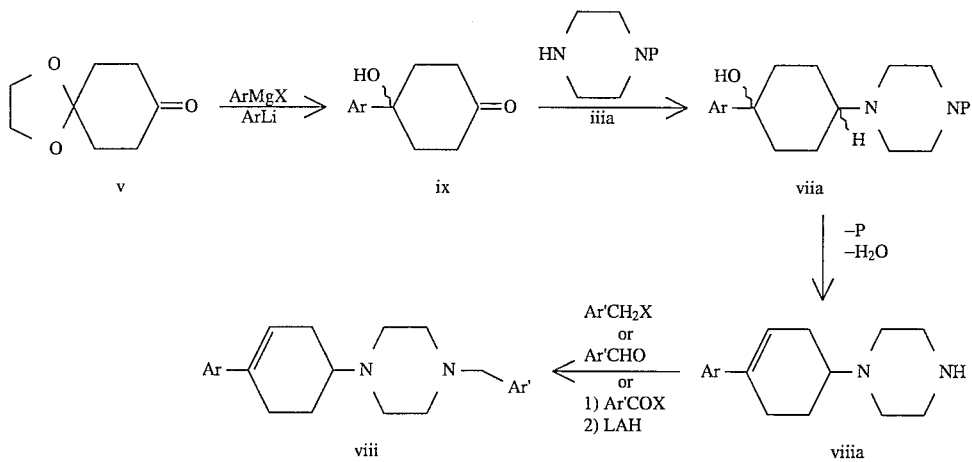

better appreciated after consideration of the following examples, which are given for the purpose of illustration only and are not be construed as limiting the invention. In the following examples, temperatures are expressed in degrees Celsius and melting points are uncorrected. Unless stated otherwise, all percentages given herein are weight percentages based on total composition weight.

The following examples describe in detail the preparation of compounds of Formula I, as well as synthetic intermediates in each process. It will be apparent to those skilled in the art that modifications, both of materials and methods, will allow preparation of other compounds disclosed herein.

A. Preparation of Intermediate Compounds

Representative procedures for preparation of synthetic intermediate compounds utilized above are given below. The starting materials and certain intermediates are either commercially available or readily available through procedures found in the chemical literature, allowing their full utilization by one skilled in the art of organic synthetic chemistry.

EXAMPLE 1

8-(4-Fluorophenyl)-1,4-dioxaspiro[4,5]decan-8-ol

A solution of 1,4-cyclohexanedione monoethylene ketal (31.2 g, 200 mmole) in dry THF (250 ml) was added to a solution of 4-fluorophenylmagnesium bromide in dry THF at −60° C. The mixture was allowed to warm to 25° C. and quenched with saturated $NH_4Cl$ solution and extracted with ether. The extracts were dried with $Na_2SO_4$ and the solvent removed in vacuo. The residue was crystallized from hexane to give the product (89%, mp: 133°–135° C.). Calc'd for $C_{14}H_{17}FO_3$: C, 66.66%; H, 6.80%. Found: C, 66.54%; H, 7.12%.

EXAMPLE 2

8-(4-Fluorophenyl)-1,4-dioxaspiro[4,5]dec-7-ene

A mixture of 8-(4-fluorophenyl)-1,4-dioxaspiro[4.5]decan-8-ol (2.0 g, 7.9 mmole) and a catalytic amount of p-toluenesulfonic acid in 50 ml toluene was heated at reflux for 1.5 hr. The mixture was cooled and washed with saturated sodium bicarbonate solution. The toluene was removed in vacuo and the residue recrystallized from hexane to give the product (81%, mp: 84°–85° C.). Calc'd for $C_{14}H_{15}FO_2$: C, 71.78%; H, 6.46%. Found: C, 71.33%; H, 6.33%.

EXAMPLE 3

8-(4-Fluorophenyl)-1,4-dioxaspiro[4.5]decane

A mixture of 8-(4-fluorophenyl)-1,4-dioxaspiro[4,5]dec-7-ene (36.7 mmole) and platinum oxide (0.15 g) was hydrogenated in ethanol for 1.5 hr. The catalyst was removed by filtration and the ethanol removed in vacuo to give the product (100%, mp: 51°–53° C.). Calc'd for $C_{14}H_{17}FO_2$: C, 71.17%; H, 7.26%. Found: C, 71.16%; H, 7.35%.

EXAMPLE 4

4-(4-Fluorophenyl)cyclohexanone

Hydrochloric acid (0.75 ml) was added to a solution 8-(4-fluorophenyl)-1,4-dioxaspiro[4,5]decane (10 mmole) in 66% methanol (100 ml). After stirring for 2 hr the methanol was removed in in vacuo and the residue extracted with methylene chloride. Removal of the methylene chloride in vacuo gave the product as an oil (87%).

EXAMPLE 5

8-(1,3-Benzodioxol-5-yl)-1,4-dioxaspiro[4,5]decan-8-ol

A solution of 1,4-cyclohexanedione monoethylene ketal in dry THF was reacted with the Grignard reagent prepared from 4-bromo-1,2-methylenedioxybenzene as described in example 1 to give the product (52%, mp: 95°–96° C.). Calc'd for $C_{15}H_{18}O_2$: C, 64.74%; H, 6.52%. Found: C, 64.41%; H, 6.41%.

EXAMPLE 6

8-(1,3-Benzodioxol-5-yl)-1,4-dioxaspiro[4,5]dec-7-ene

A solution of 8-(1,3-benzodioxol-5-yl)-1,4dioxaspiro[4.5]decan-8-ol in toluene was reacted as described in example 2 to give the product (73%, mp: 75°– 76° C.). Calc'd for $C_{15}H_{16}O_4$: C, 69.22%; H, 6.20%. Found: C, 69.19%; H, 6.14%.

EXAMPLE 7

8-(1,3-Benzodioxol-5-yl)-1,4-dioxaspiro[4,5]decane

A mixture of 8-(1,3-benzodioxol-5-yl)-1,4-dioxaspiro[4,5]dec-7-ene and 10% palladium on charcoal in ethanol was reacted as described in example 3 to give the product (91%, mp: 115°–116° C.). Calc'd for $C_{15}H_{18}O_4$: C, 68.69%; H, 6.92%. Found: C, 68.35%; H, 6.84%.

EXAMPLE 8

4-(1,3-Benzodioxol-5-yl)cyclohexanone

A solution of 8-(1,3-benzodioxol-5-yl)-1,4-dioxaspiro[4,5]decane in acetone was reacted as described in example 4 to give the product (87%, mp: 92°–93.5° C.). Calc'd for $C_{13}H_{14}O_3$: C, 71.55%; H, 6.47%. Found: C, 71.37%; H, 6.43%.

EXAMPLE 9

Cis and trans 1,1-dimethylethyl 4-[4-(4-fluorophenyl)-1-cyclohexyl]-1-piperazine Carboxylate A mixture of titanium isopropoxide (47 mmole), 4-(4-fluorophenyl)cyclohexanone (43 mmole), and 1,1-dimethylethyl 1-piperazine carboxylate (43 mmole), was stirred until no ketone absorption was observed by IR. The mixture was dissolved in ethanol (300 ml) and sodium borohydride (43 mmole) was added. After stirring for 18 hr the mixture was warmed on the steam bath and hydrolyzed by addition of 15% NaOH solution. The insoluble $TiO_2$ was removed and the solution concentrated in vacuo. The residue was suspended in water and the mixture extracted with methylene chloride. The extracts were dried and concentrated in vacuo. The crude product was mixed with 1N HCl to give the insoluble trans isomer which was the converted to the free base (47%, mp: 89°–91° C.). Calc'd for $C_{21}H_{31}FN_2O_2$: C, 69.59%; H, 8.63%; N, 7.73%. Found: C, 69.84%; H, 8.43%; N, 7.74%.

Chromatography of the mother liquor from above on silica gel eluting with methanol-methylene chloride (1:99) gave the cis isomer (8%, mp: 75°–77° C.). Calc'd for $C_{21}H_{31}FN_2O_2.0.1C_6H_{14}$: C, 69.91%; H, 8.81%; N, 7.55%. Found: C, 70.10%; H, 8.72%; N, 7.24%.

EXAMPLE 10

Trans 1-[4-(4-fluorophenyl)-1-cyclohexyl]piperazine

This compound was prepared from trans 1,1-dimethylethyl 4-[4-(4-fluorophenyl)-1-cyclohexyl]-1-piperazine carboxylate (1.7 mmole) by treatment with TFA for 0.5 hr. The TFA was removed in vacuo and the residue dissolved in water. The solution was basified with NaOH and the basic mixture extracted with methylene chloride. The extracts were dried and concentrated in vacuo to give the product which was converted to the difumarate [95%, mp: 210° C. (dec)]. Calc'd for $C_{16}H_{23}FN_2.2C_4H_3O_4.0.25H_2O$: C, 57.77%; H, 6.39%; N, 5.61%. Found: C, 57.69%; H, 6 23%; N, 5.60%.

EXAMPLE 11

Cis 1-[4-(4-fluorophenyl)-1-cyclohexyl]piperazine

This compound was prepared from cis 1,1-dimethylethyl 4-[4-(4-fluorophenyl)-1-cyclohexyl]-1-piperazine carboxylate by the method described in Example 10 to give the product as the difumarate [81%, mp: 232° C. (dec)]. Calc'd for $C_{16}H_{23}FN_2.2C_4H_4O_4.0.25H_2O$: C, 57.77%; H, 6.39%; N, 5.61%. Found: C, 57.79%; H, 6.42%; N, 5.51%.

EXAMPLE 12

Trans 1,1-dimethylethyl 4-[4-(1,3-benzodioxol-5-yl)-1-cyclohexyl]-1-piperazine Carboxylate 4-(1,3-Benzodioxol-5-yl)cyclohexanone and 1,1-dimethylethyl 1-piperazine carboxylate were reacted as described in example 9 to give the product (88%, mp: 121°–122° C.). Calc'd for $C_{22}H_{32}N_2O_4$: C, 68.01%; H, 8.31%; N, 7.22%. Found: C, 67.61%; H, 8.24%; N, 7.07%.

EXAMPLE 13

Trans phenylmethyl 4-[4-(1,3-benzodioxol-5-yl)-1-cyclohexyl]-1-piperazine Carboxylate 4-(1,3-Benzodioxol-5-yl)cyclohexanone and carbobenzyloxy piperazine were reacted as described in example 9 to give the product (31%, mp: 107°–108° C.). Calc'd for $C_{25}H_{30}N_2O_4$: C, 71.07%; H, 7.16%; N, 6.64%. Found: C, 70.95%; H, 7.16%; N, 6.36%.

EXAMPLE 14

Trans 4-[4-(1,3-benzodioxol-5-yl)-1-cyclohexyl]-1-piperazine

Method A

Trans 1,1-dimethylethyl 4-[4-(1,3-benzodioxol-5-yl)-1-cyclohexyl]-1-piperazine carboxylate was reacted as described in example 10 to give the product (93%, mp: 99°–100° C.). Calc'd for $C_{17}H_{24}N_2O_2.H_2O$: C, 66.65%; H, 8.55%; N, 9.15%. Found: C, 66.62%; H, 8.15%; N, 8.99%.

Method B

A mixture of trans phenylmethyl 4-[4-(1,3-benzodioxol-5-yl)-1-cyclohexyl]-1-piperazine carboxylate (2.0 g, 4.7 mmole) and 10% palladium on charcoal (0.5 g) in ethanol was hydrogenated until hydrogen uptake ceased. The catalyst was removed by filtration and the ethanol removed in vacuo to give the product (85%).

B. Preparation of Compounds of Formula I

EXAMPLE 15 cis 1-[(2-chlorophenyl)methyl]-4-[4-(4-fluorophenyl)-1-cyclohexyl]piperazine

The title compound was prepared by refluxing cis 1-[4-(4-fluorophenyl)-1-cyclohexyl]piperazine (0.35 g, 1.3 mmole) and 2-chlorobenzyl chloride (0.21 g, 1.3 mmole) in acetonitrile with excess potassium carbonate for 18 hr. The solvent was removed in vacuo and the crude material recrystallized from 2-propyl acetate to give the product (85%, mp: 86°–87° C.). Calc'd for $C_{23}H_{28}ClFN_2.0.4H_2O$: C, 70.09%; H, 7.37%; N, 7.11%. Found: C, 70.12%; H, 7.52%; N, 7.07%.

EXAMPLE 16

Trans 1-[(2-chlorophenyl)methyl]-4-[4-(4-fluorophenyl)-1-cyclohexyl]piperazine

The title compound was prepared from trans 1-[4-(4-fluorophenyl)-1-cyclohexyl]piperazine and 2-chlorobenzyl chloride by the method described in example 15 to give the product (44%, mp: 83°–85° C.). Calc'd for $C_{23}H_{28}ClFN_2.0.4H_2O$: C, 70.09%; H, 7.37%; N, 7.11%. Found: C, 69.99%; H, 7.38%; N, 7.07%.

EXAMPLE 17

Trans 1-[4-(4-fluorophenyl)-1-cyclohexyl]-4-[(2,5-difluorophenyl)methyl]piperazine The title compound was prepared from trans 1-[4-(4-fluorophenyl)-1-cyclohexyl]piperazine and 2,5-difluorobenzyl bromide by the method described in example 15 to give the product (69%, mp: 85°–86° C.). Calc'd for $C_{23}H_{27}F_3N_2$: C, 71.12%; H, 7.01%; N, 7.22%. Found: C, 71.11%; H, 7.01%; N, 7.19%.

EXAMPLE 18

Trans 1-[4-(1,3-benzodioxol-5-yl)-1-cyclohexyl]-4-[(3-methoxyphenyl)methyl]piperazine The title compound was prepared from trans 1-[4-(1,3-benzodioxol-5-yl)-1-cyclohexyl]piperazine and 3-methoxybenzyl chloride by the method described in example 15 to give the product (67%, mp: 93°–96° C.). Calc'd for $C_{25}H_{32}N_2O_3$: C, 73.50%; H, 7.90%; N, 6.86%. Found: C, 73.23%; H, 7.92%; N, 6.99%.

EXAMPLE 19

Trans 1-[4-(1,3-benzodioxol-5-yl)-1-cyclohexyl]-4-[(2,5-difluorophenyl)methyl]piperazine The title compound was prepared from trans 1-[4-(1,3-benzodioxol-5-yl)-1-cyclohexyl]piperazine and 2,5-difluorobenzyl bromide by the method described in example to give the product (59%, mp: 110°–111° C.). Calc'd for $C_{24}H_{28}F_2N_2O_2$: C, 69.55%; H, 6.81%; N, 6.76%. Found: C, 69.55%; H, 6.74%; N, 6.63%.

EXAMPLE 20

Trans 1-[4-(1,3-benzodioxol-5-yl)-1-cyclohexyl]-4-[(2-chlorophenyl)methyl]piperazine The title compound was prepared from trans 1-[4-(1,3-benzodioxol-5-yl)-1-cyclohexyl]piperazine and 2-chlorobenzyl chloride by the method described in example to give the product (89%, mp: 89°–90° C.). Calc'd for $C_{24}H_{29}ClN_2O_2$: C, 69.81%; H, 7.08%; N, 6.79%. Found: C, 69.50%; H, 7.03%; N, 6.71%.

EXAMPLE 21

Trans 1-[4-(1,3-benzodioxol-5-yl)-1-cyclohexyl]-4-[(2,5-difluorophenyl)methyl]piperidine 4-(1,3-Benzodioxol-5-yl)cyclohexanone and 4-(2,5-difluorobenzyl)piperidine were reacted as described in example 9 to give the product (31%, mp: 96°–97° C.). Calc'd for $C_{25}H_{29}F_2NO_2$: C, 72.61%; H, 7.07%; N, 3.39%. Found: C, 72.66%; H, 7.07%; N, 3.30%.

EXAMPLE 22

Trans 1-[4-(4-fluorophenyl)-1-cyclohexyl]-4-[(2-fluoro-5-methoxyphenyl)methyl]piperidine 4-(4-Fluorophenyl)cyclohexanone and 4-(2-fluoro-5-methoxybenzyl)piperidine were reacted as described in example 9 to give the product which was isolated as the fumarate (58%, mp: 221°–222° C.). Calc'd for $C_{25}H_{31}F_2NO \cdot C_4H_4O_4$: C, 67.56%; H, 6.85%; N, 2.72%. Found: C, 67.26%; H, 6.80%; N, 2.72%.

EXAMPLE 23

Trans 1-[4-(4-fluorophenyl)-1-cyclohexyl]-4-[(2,5-difluorophenyl)methyl]piperidine 4-(4-Fluorophenyl)cyclohexanone and 4-(2,5-difluorobenzyl)piperidine were reacted as described in example 9 to give the product (36%, mp: 80°–81° C.). Calc'd for $C_{24}H_{28}F_3N$: C, 74.40%; H, 7.29%; N, 3.18%. Found: C, 74.25%; H, 7.29%; N, 3.56%.

EXAMPLE 24

Trans 1-[4-(1,3-benzodioxol-5-yl)-1-cyclohexyl]-4-[(2-fluoro-5-methoxyphenyl)methyl]piperidine 4-(1,3-Benzodioxol-5-yl)cyclohexanone and 4-(2-fluoro-5-methoxybenzyl)piperidine were reacted as described in in example 9 to give the product (31%, mp: 89°–91° C.). Calc'd for $C_{25}H_{29}F_2NO_2$: C, 72.61%; H, 7.07%; N, 3.39%. Found: C, 72.66%; H, 7.07%; N, 3.30%.

The biological activity of the compounds prepared in Examples 15–24 is given in Table 2.

TABLE 2

| Biological Activity of Some Compounds of Formula I | | | |
|---|---|---|---|
| Example Number | $D_2$, nM | Sigma, nm | Anoxia, % p 10 mg/kg |
| 15 | 462 | 3.2 | |
| 16 | 432 | 3.5 | 100 |
| 17 | 261 | 1.5 | 50 |
| 18 | 511 | 1.5 | 75 |
| 19 | 140 | | 50 |
| 20 | 352 | | 75 |
| 21 | 336 | | 88 |
| 22 | 835 | | |
| 23 | 501 | | |
| 24 | 884 | | |

Reasonable variations, such as those which would occur to a skilled artisan, can be made herein without departing from the scope of the invention.

We claim:

1. A dopaminergic compound of Formula I or a pharmaceutically acceptable salt or hydrate thereof:

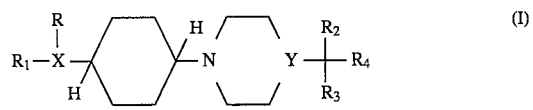

wherein

R=$R_1$ and is independently H or halogen; or R and $R_1$ may be taken together to form an —O(CH$_2$)$_m$O— (m=1 or 2);

X=phenyl;

Y=N or CH;

$R_2$=$R_3$ and is independently H or $C_{1-4}$ alkyl; and $R_4$=phenyl or substituted phenyl wherein the phenyl group is mono-, or di-substituted with groups selected from: F, Cl, I and $C_{1-4}$ alkoxy.

2. The compound of claim 1 wherein $R_2$ and $R_3$ are both H.

3. The compound of claim 2 wherein $R_4$ is a mono- or disubstituted phenyl moiety.

4. The compound of claim 3 selected from the group consisting of:

cis 1-[(2-chlorophenyl)methyl]-4-[4-(4-fluorophenyl)-1-cyclohexyl]piperazine;

trans 1-[(2-chlorophenyl)methyl]-4-[4-(4-fluorophenyl)-1-cyclohexyl]piperazine;

trans 1-[4-(4-fluorophenyl)-1-cyclohexyl]-4-[(2,5-difluorophenyl)methyl]piperazine;

trans 1-[4-(1,3-benzodioxol-5-yl)-1-cyclohexyl]-4-[(3-methoxyphenyl)methyl]piperazine;

trans 1-[4-(1,3-benzodioxol-5-yl)-1-cyclohexyl]-4-[(2,5-difluorophenyl)methyl]piperazine;

trans 1-[4-(1,3-benzodioxol-5-yl)-1-cyclohexyl]-4-[(2-chlorophenyl)methyl]piperazine;

trans 1-[4-(1,3-benzodioxol-5-yl)-1-cyclohexyl]-4-[(2,5-difluorophenyl)methyl]piperidine;

trans 1-[4-(4-fluorophenyl)-1-cyclohexyl]-4-[(2-fluoro-5-methoxyphenyl)methyl]piperidine;

trans 1-[4-(4-fluorophenyl)-1-cyclohexyl]-4-[(2,5-difluorophenyl)methyl]piperidine; and trans 1-[4-(1,3-benzodioxol-5-yl)-1-cyclohexyl]-4-[(2-fluoro-5-methoxyphenyl)methyl]piperidine.

5. A pharmaceutical composition comprising an effective antiischemia amount of a compound of claim 1 and a pharmaceutically acceptable carrier.

6. The composition of claim 5 wherein the compound is one in which $R_2$ and $R_3$ are both H.

7. The composition of claim 6 wherein the compound is one in which $R_4$ is a mono- or disubstituted phenyl moiety.

8. The composition of claim 5 wherein the compound is selected from the group consisting of:

cis 1-[(2-chlorophenyl)methyl]-4-[4-(4-fluorophenyl)-1-cyclohexyl]piperazine;

trans 1-[(2-chlorophenyl)methyl]-4-[4-(4-fluorophenyl)-1-cyclohexyl]piperazine;

trans 1-[4-(4-fluorophenyl)-1-cyclohexyl]-4-[(2,5-difluorophenyl)methyl]piperazine;

trans 1-[4-(1,3-benzodioxol-5-yl)-1-cyclohexyl]-4-[(3-methoxyphenyl)methyl]piperazine;

trans 1-[4-(1,3-benzodioxol-5-yl)-1-cyclohexyl]-4-[(2,5-difluorophenyl)methyl]piperazine;

trans 1-[4-(1,3-benzodioxol-5-yl)-1-cyclohexyl]-4-[(2chlorophenyl)methyl]piperazine;

trans 1-[4-(1,3-benzodioxol-5-yl)-1-cyclohexyl]-4-[(2,5-difluorophenyl)methyl]piperidine;

trans 1-[4-(4-fluorophenyl)-1-cyclohexyl]-4-[(2-fluoro-5-methoxyphenyl)methyl]piperidine;

trans 1-[4-(4-fluorophenyl)-1-cyclohexyl]-4-[(2,5-difluorophenyl)methyl]piperidine; and trans 1-[4-(1,3-benzodioxol-5-yl)-1-cyclohexyl]-4-[(2-fluoro-5-methoxyphenyl)methyl]piperidine.

9. A process for treating ischemia-induced disorders in a mammal in need of such treatment, the treatment comprising administering to the mammal an effective amount of a compound of claim 1.

10. The process of claim 9 wherein the compound is one in which $R_2$ and $R_3$ are both H.

11. The process of claim 10 wherein the compound is one in which $R_4$ is a mono- or disubstituted phenyl moiety.

12. The process of claim 9 wherein the compound is selected from the group consisting of:

cis 1-[(2-chlorophenyl)methyl]-4-[4-(4-fluorophenyl)-1-cyclohexyl]piperazine;

trans 1-[(2-chlorophenyl)methyl]-4-[4-(4-fluorophenyl)-1-cyclohexyl]piperazine;

trans 1-[4-(4-fluorophenyl)-1-cyclohexyl]-4-[(2,5-difluorophenyl)methyl]piperazine;

trans 1-[4-(1,3-benzodioxol-5-yl)-1-cyclohexyl]-4-[(3-methoxyphenyl)methyl]piperazine;

trans 1-[4-(1,3-benzodioxol-5-yl)-1-cyclohexyl]-4-[(2,5-difluorophenyl)methyl]piperazine;

trans 1-[4-(1,3-benzodioxol-5-yl)-1-cyclohexyl]-4-[(2-chlorophenyl)methyl]piperazine;

trans 1-[4-(1,3-benzodioxol-5-yl)-1-cyclohexyl]-4-[(2,5-difluorophenyl)methyl]piperidine;

trans 1-[4-(4-fluorophenyl)-1-cyclohexyl]-4-[(2-fluoro-5-methoxyphenyl)methyl]piperidine;

trans 1-[4-(4-fluorophenyl)-1-cyclohexyl]-4-[(2,5-difluorophenyl)methyl]piperidine; and trans 1-[4-(1,3-benzodioxol-5-yl)-1-cyclohexyl]-4-[(2-fluoro-5-methoxyphenyl)methyl]piperidine.

* * * * *